(12) United States Patent
Miura et al.

(10) Patent No.: US 8,921,574 B2
(45) Date of Patent: Dec. 30, 2014

(54) METHOD FOR PRODUCING PYRAZOLINONE SALT

(75) Inventors: Masaya Miura, Oita (JP); Masao Kojio, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 53 days.

(21) Appl. No.: 13/881,199

(22) PCT Filed: Nov. 1, 2011

(86) PCT No.: PCT/JP2011/075648
§ 371 (c)(1),
(2), (4) Date: Apr. 24, 2013

(87) PCT Pub. No.: WO2012/063791
PCT Pub. Date: May 18, 2012

(65) Prior Publication Data
US 2013/0217890 A1    Aug. 22, 2013

(30) Foreign Application Priority Data
Nov. 12, 2010  (JP) .................................. 2010-253567

(51) Int. Cl.
*C07D 231/52*    (2006.01)

(52) U.S. Cl.
CPC ..................................... *C07D 231/52* (2013.01)
USPC ...................................................... 548/368.7

(58) Field of Classification Search
None
See application file for complete search history.

(56) References Cited

U.S. PATENT DOCUMENTS

| | | |
|---|---|---|
| 5,175,313 A | 12/1992 | Imuta et al. |
| 5,869,684 A | 2/1999 | Hashizume et al. |
| 6,294,567 B1 | 9/2001 | Hashizume et al. |
| 2012/0071666 A1 | 3/2012 | Hatano et al. |

FOREIGN PATENT DOCUMENTS

| | | |
|---|---|---|
| JP | 04-013674 A | 1/1992 |
| JP | 2002-316902 A | 10/2002 |
| WO | 9954307 A1 | 10/1999 |
| WO | 2010143598 A1 | 12/2010 |

OTHER PUBLICATIONS

Int'l Search Report issued Dec. 27, 2011 in Int'l Application No. PCT/JP2011/075648.
Int'l Preliminary Rerport on Patentability issued May 23, 2013 in Int'l Application No. PCT/JP2011/075648.

*Primary Examiner* — Kamal Saeed
(74) *Attorney, Agent, or Firm* — Panitch Schwarze Belisario & Nadel LLP

(57) ABSTRACT

A salt represented by formula (4) produced via
 a first step of dehydrating a mixture containing a hydrocarbon solvent and an alkali metal hydroxide represented by formula: $A^+ OH^-$, and
 a second step or reacting the mixture dehydrated in the first step with a compound represented by formula (2) is useful for producing an active ingredient of a plant disease control agent.

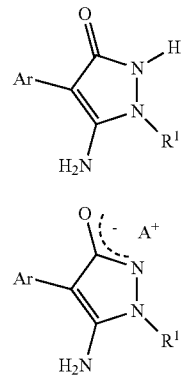

10 Claims, 1 Drawing Sheet

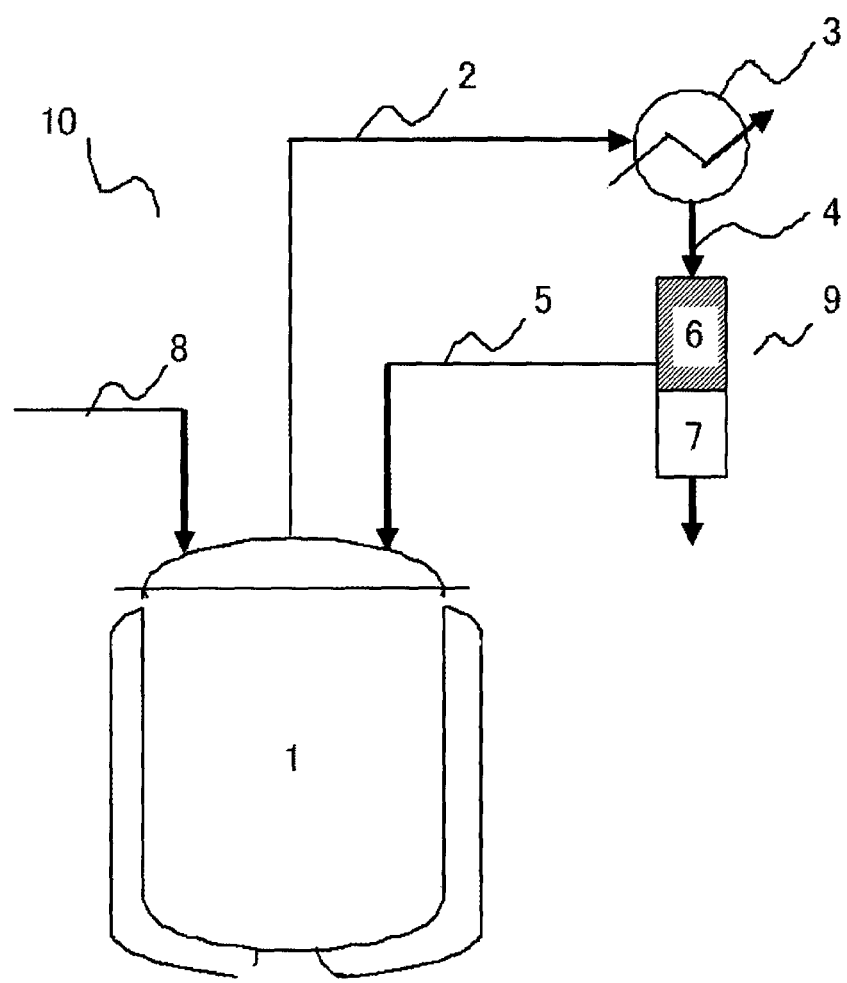

METHOD FOR PRODUCING PYRAZOLINONE SALT

CROSS-REDERENCE TO RELATED APPLICATION

This application is a Section 371 of International Application No. PCT/JP2011/0756848, filed on Nov. 1, 2011, which was published in the Japanese language on May 18, 2012, under Internation Pulication No. WO 2012/063791 A1, and the disclosure of which is incorporated herein by reference.

TECHNICAL FIELD

The present invention relates to a method for producing a pyrazolinone salt.

BACKGROUND ART

In U.S. Pat. No. 6,294,567, a certain kind of pyrazolinone compound is known to be useful as an active ingredient of a plant disease control agent.

U.S. Pat. No. 5,869,684 describes a method for producing a compound represented by formula (1A):

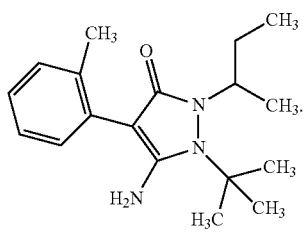

(1A)

DISCLOSURE OF THE INVENTION

The present invention provides a method which is capable of producing a pyrazolinone derivative with excellent yield.

The present invention is as described below.

<1> A method for producing a salt represented by formula (4):

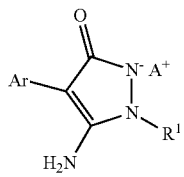

(4)

wherein $A^+$ represents an alkali metal cations, Ar represents an optionally substituted phenyl group, $R^1$ represents an optionally substituted hydrocarbon group, and —$CH_2$— contained in the hydrocarbon group may be replaced by a hetero atom or a carbonyl group, the method comprising a first step of dehydrating a mixture containing a hydrocarbon solvent and an alkali metal hydroxide represented by the following formula:

$A^+OH^-$ wherein $A^+$ has the same meaning as described above, wherein the mixture contains no compound represented by the following formula (2), and a second step of reacting the mixture dehydrated in the first step with a compound represented by formula (2):

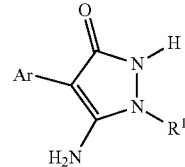

(2)

wherein Ar and $R^1$ have the same meanings as described above.

<2> The method according to <1>, wherein the second step is a step of reacting the mixture dehydrated in the first step with a compound represented by formula (2) while performing dehydration.

<3> The method according to <2>, wherein the second step is a step of reacting the mixture dehydrated in the first step with a compound represented by formula (2) while adjusting the amount of water contained in the reaction solution in the second step to 0.8 wt % or less.

<4> The method according to <2> or <3>, wherein the second step is a step of reacting the mixture dehydrated in the first step with a compound represented by formula (2) while performing azeotropic dehydration under reduced pressure at a temperature in the range of 20 to 100° C.

<5> The method according to any one of <1> to <4>, wherein the amount of water contained in the mixture dehydrated in the first step is 0.8 wt % or less.

<6> The method according to any one of <1> to <5>, wherein the first step is a step of performing azeotropic dehydration under reduced pressure at a temperature in the range of 20 to 100° C.

<7> The method according to any on of <1> to <6>, wherein the alkali metal hydroxide is lithium hydroxide.

<8> The method according to any one of <1> to <7>, wherein the hydrocarbon solvent is an aromatic hydrocarbon solvent.

<9> The method according to any one of <1> to <8>, wherein the second step is a step of reacting the mixture dehydrated in the first step with a compound represented by formula (2) in the presence of an ether solvent.

<10> A method for producing a pyrazolinone derivative represented by formula (1):

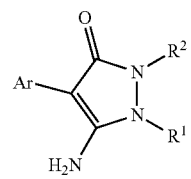

(1)

wherein Ar represents an optionally substituted phenyl group, $R^1$ represents an optionally substituted hydrocarbon group, —$CH_2$— contained in the hydrocarbon group may be replaced by a hetero atom or a carbonyl group, and $R^2$ represents an optionally substituted hydrocarbon group, the method comprising a first step of dehydrating a mixture containing a hydrocarbon solvent and an alkali metal hydroxide represented by the following formula:

$A^+OH^-$ wherein $A^+$ represents an alkali metal cation, wherein the mixture contains no compound represented by the following formula (2), a second step of reacting the mixture dehydrated in the first step with a compound represented by formula (2):

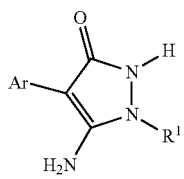

(2)

wherein Ar and $R^1$ have the same meanings as described above, and a third step of reacting the product obtained in the second step with a compound represented by formula (3);

$$R^2—O—SO_2R^3 \quad (3)$$

wherein $R^2$ has the same meaning as described above and $R^3$ represents an optionally substituted phenyl group or an alkyl group having 1 to 10 carbon atoms.

BRIEF EXPLANATION OF DRAWING

FIG. 1 shows an example of a reaction apparatus used for a first step and a second step.

MODES FOR CARRYING OUT THE INVENTION

The method for producing a salt represented by formula (4) (hereinafter, referred to as salt (4) in some cases) will be explained.

The method for producing salt (4) has a first step and a second step.

The first step is a step of dehydrating a mixture containing a hydrocarbon solvent and an alkali metal hydroxide represented by the following formula:

$$A^+ \ OH^-$$

wherein $A^+$ represents an alkali metal cation, wherein the mixture contains no compound represented by the following formula (2).

Examples of the hydrocarbon solvent used in the first step includes aliphatic hydrocarbons such as normal pentane, normal hexane and normal heptane, alicyclic hydrocarbons such as cyclopentane and cyclohexane and aromatic hydrocarbons such as benzene, toluene, xylene and chlorobenzene. The hydrocarbon solvent used in the first step includes preferably aromatic hydrocarbons, more preferably toluene and xylene.

The use amount of the hydrocarbon solvent in the first step is usually in the range of 0.1 to 1000 parts by weight, preferably 1 to 50 parts by weight with respect to 1 part by weight of an alkali metal hydroxide.

The first step may be carried out in the presence of an ether solvent in addition to the hydrocarbon solvent.

Examples of the ether solvent which can be used in the first step include dialkyl ethers having 2 to 20 carbon atoms such as diethyl ether, cyclic ethers having 5 to 12 ring constituent atoms such as tetrahydrofuran, 1,3-dioxane and 1,4-dioxane, and (poly)alkylene glycol dialkyl ethers having 4 to 12 carbon atoms such as diethylene glycol dimethyl ether, diethylene glycol diethyl ether and dipropylene glycol dimethyl ether. The ether solvent which can be used in the first step includes preferably cyclic ethers having 5 to 13 ring constituent atoms, more preferably tetrahydrofuran.

When the ether solvent is used in the first step, the use amount of the ether solvent is usually 1 part by weight or less, preferably 0.25 parts by weight or less with respect to 1 part by weight of a hydrocarbon solvent.

Examples of the alkali metal hydroxide used in the first step includes lithium hydroxide, sodium hydroxide and potassium hydroxide. The alkali metal hydroxide used in the first step includes preferably lithium hydroxide. The alkali metal hydroxide may be an aqueous solution or a hydrate.

Water contained in a hydrocarbon solvent, water contained in an alkali metal hydroxide (also including water of a hydrate) and water adhered to a reaction tank and the like used for the dehydration in the first step and dehydrated in the first step. The amount of water contained in a mixture aster completion of the first step (hereinafter, referred to as mixture [1] in some cases) is preferably 0.8 wt % or less, more preferably 0.5 wt % or less.

Specific examples of the first step include a method in which from a reaction tank containing a mixed solution including an alkali metal hydroxide and a hydrocarbon solvent, a hydrocarbon solvent containing water is distilled at normal pressure or under reduced pressure at a temperature in the range of 20° C. to 100° C., preferably in the range of 40° C. to 80° C., and a hydrocarbon solvent having water content adjusted to 0.8 wt % or less, preferably 0.5 wt % or less is separately mixed (hereinafter, referred to as method A in some cases), a method in which the hydrocarbon solvent distilled in the same manner as described above from the reaction tank is separated, and the hydrocarbon solvent having reduced water is refluxed to the reaction tank (hereinafter, referred to as method B in some cases). When the first step is carried out by method B, it is preferable to carry out the method under reduced pressure for refluxing in the above-described temperature range.

The content of a hydrocarbon solvent contained in a mixture of an alkali metal hydroxide and the hydrocarbon solvent obtained in the first step is usually 0.1 to 1000 parts by weight, preferably 1 to 50 parts by weight with respect to 1 part by weight of the alkali metal hydroxide.

The treatment time of the first step is not particularly restricted providing that the water content is adjusted to 0.8 wt % or less. The treatment time of the first step is usually in the range of 1 to 24 hours.

From the viewpoint of the yield of salt (4) and derivative (1), the reaction solution of the first step does not contain compound (2). The reaction solution of the first step does not contain compound (2) means that the content of compound (2) contained in the reaction solution of the first step is 5 parts by weight or less, preferably 1 part by weight or less, more preferably 0.1 part by weight or less with respect to 100 parts by weight compound (2) used in the second step described later.

The second step is a step of reacting the mixture dehydrated in the first step with a compound represented by formula (2):

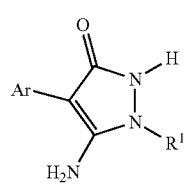

(2)

wherein Ar represents an optionally substituted phenyl group and $R^1$ represents an optionally substituted hydrocarbon group, and —CH₂— contained in the hydrocarbon group may be replaced by a hetero atom or a carbonyl group, namely, compound (2).

Ar in compound (2) represents an optionally substituted phenyl group such as phenyl groups represented by formula (5):

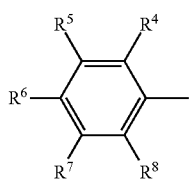

(5)

R⁴ and R⁸ in formula (5) represent each independently a hydrogen atom, a halogen atom, an alkyl group, a haloalkyl group, an alkoxy group, an alkoxyalkyl group, a haloalkoxy group, an alkylthio group, a haloalkylthio group, a cyano group, a nitro group, an optionally substituted phenyl group or an optionally substituted phenoxy group, alternatively, two adjacent moieties of R⁴ to R⁸ are linked at ends to represent a group represented by —CH═CH—CH═CH—, a methylenedioxy group optionally having a halogen atom or an alkylene group optionally having an alkyl group. A methylene group (—CH₂—) contained in the alkylene group may be replaced by an oxygen atom (—O—).

Examples of the halogen atom represented by R⁴ to R⁸ include a fluorine atom, a chlorine atom, a bromine atom and an iodine atom.

The alkyl group represented by R⁴ and R⁸ includes, for example, linear or branched alkyl groups having 1 to 5 carbon atoms (hereinafter, referred to as C1 to C5 in some cases), and specific examples thereof include a methyl group, an ethyl group, a normal propyl group, an isopropyl group and a t-butyl group. The haloalkyl group means a group obtained by substituting part or all of hydrogen atoms of the above-described alkyl group by a halogen atom. The haloalkyl group represented by R⁴ to R⁸ includes, for example, linear or branched C1 to C5 alkyl groups having 1 to 11 halogen atoms in the haloalkyl group, and specific examples thereof include a trifluoromethyl group, a tetrafluoroethyl group and a heptafluoropropyl group.

The alkoxy group represented by R⁴ to R⁸ includes, for example, linear or branched C1 to C5 alkoxy groups, and specific examples thereof include a methoxy group, an ethoxy group, a normal propyloxy group and an isopropyloxy group. The alkoxyalkoxy group represented by R⁴ to R⁸ includes, for example, linear or branched (C1 to C3) alkoxy (C1 to C3) alkoxy groups, and specific examples thereof include a methoxymethoxy group. The haloalkoxy group represented by R⁴ to R⁸ includes, for example, linear or branched C1 to C5 alkoxy groups substituted by identical or mutually different 1 to 11 halogen atoms, and specific examples thereof include a trifluoromethoxy group, a difluoromethoxy group and a tetrafluoroethoxy group.

The alkylthio group represented by R⁴ to R⁸ includes, for example, linear or branched C1 to C5 alkylthio groups, and specific examples thereof include a methylthio group and an ethylthio group. The haloalkylthio group represented by R⁴ to R⁸ includes, for example, linear or branched C1 to C5 alkylthio groups substituted by identical or mutually different 1 to 11 halogen atoms, and specific examples thereof include a trifluoromethylthio group.

The optionally substituted phenyl group represented by R⁴ and R⁸ means a phenyl group optionally having identical or mutually different 1 to 5 substituents. The optionally substituted phenoxy group represented by R⁴ and R⁸ means a phenoxy group optionally having identical or mutually different 1 to 5 substituents. The substituent on the phenyl group or phenoxy group includes, for example, halogen atoms (a fluorine atom, a chlorine atom, a bromine atom and an iodine atom), C1 to C5 alkyl groups (for example, a methyl group and an ethyl group), C1 to C5 alkoxy groups (for example, a methoxy group and an ethoxy group), C1 to C5 alkylthio groups (for example, a methylthio group and an ethylthio group), C1 to C5 haloalkyl groups (for example, C1 to C2 haloalkyl groups such as a trifluoromethyl group), C1 to C5 haloalkoxy groups (for example, C1 to C2 haloalkoxy groups such as a trifluoromethoxy group and a difluoromethoxy group), C1 to C5 haloalkylthio groups (for example, C1 to C2 haloalkylthio groups such as a trifluoromethylthio group) and a cyano group.

The methylenedioxy group optionally having a halogen atom represented by R⁴ to R⁸ includes, for example, a methylenedioxy group an a difluoromethylenedioxy group.

The alkylene group (for example, C2 to C6 alkylene groups) optionally having an alkyl group (for example, C1 to C4 alkyl groups such as a methyl group) represented by R⁴ to R⁸ includes, for example, a trimethylene group and a tetramethylene group. The alkylene group obtained by substituting a methylene group contained in the alkylene group by an oxygen atom includes, for example, a group represented by —OCH₂CH₂Cl and a group represented by OCH₂CH(CH₃)Cl.

Ar includes preferably a phenyl groups, an o-tolyl group, a 2,6-dimethylphenyl group, a 2-chlorophenyl group and a 2,6-dichlorophenyl group.

The optionally substituted hydrocarbon group represented by R¹ includes, for example, linear or branched C1 to C10 alkyl groups (for example, a methyl group, an ethyl group, a propyl group, an isopropyl group, a butyl group, an isobutyl group, a secondary butyl group, a 2-methylbutyl group, a 2-ethylpropyl group and a t-butyl group);

linear or branched C2 to C10 alkenyl groups (for example, a 1-methyl-2-propenyl group);

linear or branched C2 to C10 alkynyl groups (for example, a 1-methyl-2-propynyl group);

linear or branched C1 to C10 alkyl groups substituted by identical or mutually different 1 to 21 halogen atoms;

linear or branched C2 to C10 alkenyl groups substituted by identical or mutually different 1 to 19 halogen atoms;

linear or branched C2 to C10 alkynyl groups substituted by identical or mutually different 1 to 17 halogen atoms;

C1 to C5 alkyl groups having a linear or branched C1 to C5 alkoxy (for example, a methoxymethyl group and a 1-methyoxyethyl group);

C1 to C5 alkyl groups having a linear or branched C1 to C5 alkylthio group (for example, a methylthiomethyl group and a 1-methylthioethyl group);

linear or branched C1 to C5 alkyl groups having a C1 to C5 alkoxy group having identical or mutually different 1 to 11 halogen atoms and having identical or mutually different 1 to 10 halogen atoms;

linear or branched C1 to C5 alkyl groups having a C1 to C5 alkylthio group having identical or mutually different 1 to 11 halogen atoms and having identical or mutually different 1 to 10 halogen atoms;

linear or branched C1 to C5 alkyl groups having a cyano group (for example, a 1-cyanoethyl group);

linear or branched C1 to C5 alkyl groups having a C1 to C5 alkoxycarbonyl group (for example, a 1-(methoxycarbonyl) ethyl group);

C3 to C8 cycloalkyl groups optionally having a halogen atom and optionally containing an unsaturated bond (for example, a cyclohexyl group and a cyclopentyl group);

C2 to C6 alkylcarbonyl groups (for example, an acetyl group, a propanoyl group, a butanoyl group and a pentanoyl group);

C3 to C6 alkenylcarbonyl groups (for example, a 3-butenoyl group);

C2 to C6 alkoxycarbonyl groups (for example, a methoxycarbonyl group, an ethoxycarbonyl group and a propyloxycarbonyl group);

C3 to C6 alkenyloxycarbonyl groups (for example, an allyloxycarbonyl group);

C2 to C6 alkylthiocarbonyl groups (for example, a methylthiocarbonyl group, an ethylthiocarbonyl group and a propylthiocarbonyl group);

C3 to C6 alkenylthiocarbonyl groups (for example, an allylthiocarbonyl group);

phenyl groups optionally having identical or mutually different 1 to 5 substituents {examples of the substituent include halogen atoms (a fluorine atom, a chlorine atom, a bromine atom and an iodine atom), C1 to C5 alkyl groups (for example, a methyl group and an ethyl group), C1 to C5 alkoxy groups (for example, a methoxy group and an ethoxy group), C1 to C5 alkylthio groups (for example, a methylthio group and an ethylthio group), C1 to C5 haloalkyl groups (for example, C1 to C2 haloalkyl groups such as a trifluoromethyl group), C1 to C5 haloalkoxy groups (for example, C1 to C2 haloalkoxy groups such as a trifluoromethoxy group and a difuloromethoxy group), C1 to C5 haloalkylthio groups (for example, C1 to C2 haloalkylthio groups such as a trifluoromethylthio group) and a cyano group}; and C7 to C17 aralkyl groups optionally having identical or mutually different 1 to 5 substituents (for example, a benzyl group, an α-methylbenzyl group and an α,α-dimethylbenzyl group) {examples of the substituent include halogen atoms (a fluorine atom, a chlorine atom, a bromine atom and an iodine atom), C1 to C5 alkyl groups (for example, a methyl group and an ethyl group), C1 to C5 alkoxy groups (for example, a methoxy group and an ethoxy group), C1 to C5 alkylthio groups (for example, a methylthio group and an ethylthio group), C1 to C5 haloalkyl groups (for example, C1 to C2 haloalkyl groups such as a trifluoromethyl group), C1 to C5 haloalkoxy groups (for example, C1 to C2 haloalkoxy groups such as a trifluoromethoxy group and a difluoromethoxy group), C1 to C5 haloalkylthio groups (for example, C1 to C2 haloalkylthio groups such as a trifluoromethylthio group), and a cyano group.}.

Compound (2) includes, for example, compounds described in Table 1.

TABLE 1

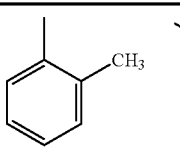

| Compound number | —Ar | —R¹ |
|---|---|---|
| (2-1) | 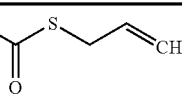 | |

TABLE 1-continued

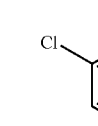

| Compound number | —Ar | —R¹ |
|---|---|---|
| (2-2) | 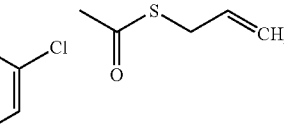 | |

Compound (2) is dissolved in, for example, a hydrocarbon solvent and/or an ether solvent, preferably a mixed solvent of a hydrocarbon solvent and an ether solvent and the resultant solution is added to mixture [1]. As the hydrocarbon solvent and the ether solvent used in this case, the same solvents as described above are exemplified, respectively.

The second step is carried out preferably in the presence of a mixed solvent of a hydrocarbon solvent and an ether solvent, more preferably in the presence of a mixed solvent of a hydrocarbon solvent and tetrahydrofuran.

When the second step is carried out in the presence of a mixed solvent of a hydrocarbon solvent and an ether solvent, the weight ration of the hydrocarbon solvent to the ether solvent is usually in the range of 1 to 5 parts by weight with respect to 1 part by weight of the ether solvent. The use amount of the hydrocarbon solvent in the second step is usually in the range of 0.1 to 1000 parts by weight, preferably in the range of 1 to 10 parts by weight with respect to 1 part by weight of compound (2).

Since water is generated by reaction of compound (2) and an alkali metal hydroxide, it is preferable that the reaction is conducted while performing dehydration in the second step. Specifically mentioned is a method of mixing compound (2) and mixture [1] under reduced pressure at a temperature in the range of 20 to 100° C., preferably of 40 to 80° C.

From the viewpoint of the yield of salt (4) and derivative (1), it is preferable that the water content of the reaction solution in the second step is adjusted to 0.8 wt % or less, preferably 0.5 wt % or less by performing dehydration.

The water content of the reaction solution in the second step can be easily adjusted to 0.8 wt % or less, preferably 0.5 wt % or less by gradually mixing mixture [1] and compound (2).

The reaction time of the second step is not particularly restricted providing that the water content of mixture [1] is adjusted to 0.8 wt % or less, preferably 0.5 wt % or less. The reactoin time of the second step is usually in the range of 1 to 18 hours.

Specific examples of the second step include a method <2-I> in which compound (2) is mixed into mixture [1] while dehydrating under reflux a hydrocarbon solvent; a method <2-II> in which mixture [1] and compound (2) are concurrently mixed while dehydrating under reflux a hydrocarbon solvent; and a method <2-III> in which mixture [1] is mixed into a solution containing compound (1) while dehydrating under reflux a hydrocarbon solvent. It is preferable that the second step in the present invention is carried out according to the method <2-I>.

When the first step and the second step of the present invention are carried out, a solution containing a salt represented by formula (4):

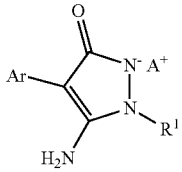
(4)

wherein $A^+$, Ar and $R^1$ have the same meanings as described above,
(hereinafter, referred to as salt (4) in some cases) is obtained.

According to the present invention, generation of a salt in which $R^1$ of compound (2) is rearranged to a nitrogen atom at the α-position of a carbonyl group, namely, a salt represented by formula (4'):

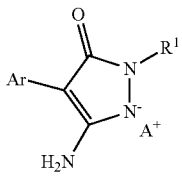
(4')

wherein $A^+$, Ar and $R^1$ have the same meaning as described above,
is suppressed.

It is guessed that not only a salt having a structure represented by formula (4) but also a salt having a structure represented by formula (4"):

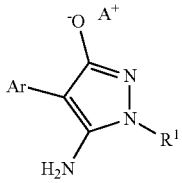
(4")

wherein $A^+$, Ar and $R^1$ have the same meaning as described above,
namely, a tautomer of salt (4) are present in a solution containing salt (4), and as described above, when water is mixed into a solution obtained by carrying out the first step and the second step, compound (2) can be obtained with good yield and when a third step described later is carried out on the solution, derivative (1) can be obtained with good yield.

By carrying out a step of reacting a solution containing salt (4) with a compound represented by formula (3):

$R^2$—O—$SO_2R^3$ (3)

wherein $R^2$ represents an optionally substituted hydrocarbon group and $R^3$ represents an optionally substituted phenyl group or an alkyl group having 1 to 10 carbon atoms, (hereinafter, referred to as compound (3) in some cases) (hereinafter, referred to as third step in some cases), a pyrazolinone derivative represented by formula (1):

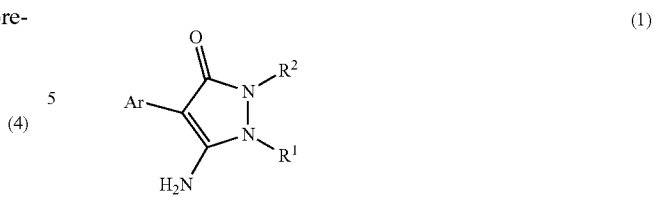
(1)

wherein Ar, $R^1$ and $R^2$ have the same meaning as described above,
is obtained.

The optionally substituted hydrocarbon group represented by $R^2$ in compound (3) includes, for example,
linear or branched C1 to C10 alkyl groups (for example, an ethyl group, a propyl group, an isopropyl group, a butyl group, an isobutyl group, a secondary butyl group, a 2-methylbutyl group and a 2-ethylpropyl group);
linear or branched C2 to C10 alkenyl groups (for example, a 1-methyl-2-propenyl group);
linear or branched C2 to C10 alkynyl groups (for example, a 1-methyl-2-propynyl group);
linear or branched C1 to C10 alkyl groups having identical or mutually different 1 to 21 halogen atoms;
linear or branched C2 to C10 alkenyl groups having identical or mutually different 1 to 19 halogen atoms;
linear or branched C2 to C10 alkynyl groups having identical or mutually different 1 to 17 halogen atoms;
C1 to C5 alkyl groups having a linear or branched C1 to C5 alkoxy (for example, a 1-methyl-21-methoxyethyl group);
C1 to C5 alkyl groups having a linear or branched C1 to C5 alkylthio group (for example, a 1-methyl-2-methylthioethyl group);
linear or branched C1 to C5 alkyl groups having a C1 to C5 alkoxy group having identical or mutually different 1 to 11 halogen atoms and substituted by identical or mutually different 1 to 10 halogen atoms;
linear or branched C1 to C5 alkyl groups having a C1 to C5 alkylthio group having identical or mutually different 1 to 11 halogen atoms and having identical or mutually different 1 to 10 halogen atoms;
linear or branched C1 to C5 alkyl groups substituted by a cyano group (for example, a 1-methyl-2-cyanoethyl group);
linear or branched C1 to C5 alkyl groups having a C1 to C5 alkoxycarbonyl group (for example, a 2-methyoxycarbonyl-ethyl group);
C3 to C8 cycloalkyl groups optionally having a halogen atom and optionally containing an unsaturated bond (for example, a cyclohexyl group and a cyclopentyl group); and
C7 to C17 aralkyl groups optionally substituted by identical or mutually different 1 to 5 substituents (for example, a benzyl group and an α-methylbenzyl group) {examples of the substituent include a halogen atoms (a fluorine atom, a chlorine atom, a bromine atom and an iodine atom), C1 to C5 alkyl groups (for example, a methyl group and an ethyl group), C1 to C5 alkoxy groups (for example, a methoxy group and an ethoxy group), C1 to C5 alkylthio groups (for example, a methylthio group and an ethylthio group), C1 to C5 haloalkyl groups (for example, C1 to C2 haloalkyl groups such as a trifluoromethyl group), C1 to C5 haloalkoxy groups (for example, C1 to C2 haloalkoxy groups such as a trifluoromethoxy group and a difluoromethoxy group), C1 to C5 haloalkylthio groups (for example, C1 to C2 haloalkylthio groups such as a trifluoromethylthio group), and a cyano group.}.

Examples of the C1 to C10 alkyl group represented by $R^3$ include a methyl group, an ethyl group, a normal propyl group, an isopropyl group and a t-butyl group. Examples of the optionally substituted phenyl group represented by $R^3$ include a phenyl group, a 2-methylphenyl group, a 3-methylphenyl group, a 4-methylphenyl group, a 2-methoxyphenyl group, a 3-methoxyphenyl group, a 4-methoxyphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group and a 4-bromophenyl group.

Compound (3) includes, for example, compounds described in Table 2.

TABLE 2

$R^2-O-SO_2R^3$ (3)

| Compound number | $-R^2$ | $-R^3$ |
|---|---|---|
| (3-1) | $-CH(CH_3)_2$ | $-CH_3$ |
| (3-2) | $-C(CH_3)_3$ | $-CH_3$ |
| (3-3) | $-CH_3$ | $-CH_3$ |
| (3-4) | $-CH(CH_3)_2$ | $-C_2H_5$ |
| (3-5) | $-C(CH_3)_3$ | $-C_2H_5$ |
| (3-6) | $-CH_3$ | $-C_2H_5$ |
| (3-7) | $-CH(CH_3)_2$ | 4-methylphenyl |
| (3-8) | $-C(CH_3)_3$ | 4-methylphenyl |
| (3-9) | $-CH_3$ | 4-methylphenyl |

Regarding the mixing proportion of salt (4) and compound (3), the amount of compound (3) is, for example, in the range of 0.9 to 1.5 mol with respect to 1 mol of compound (2) used for preparation of salt (4).

The reaction temperature of the third step is usually in the range of 40° C. to 120° C., preferably in the range of 60° C. to 100° C.

Specific examples of the third step include a method <3-I> in which a solution containing compound (3) is mixed into a solution containing salt (4); a method <3-II> in which a solution containing salt (4) and a solution containing compound (3) are concurrently mixed into a hydrocarbon solvent and/or an ether solvent; and a method <3-III> in which a solution containing salt (4) is mixed into a solution containing compound (3). The third step is carried out preferably according to the method <3-II>.

With respect to progress of the reaction in the third step, it is preferable that the consumption amount of compound (3) is confirmed by a means such as gas chromatography and high performance liquid chromatography and the reaction is continued until no consumption of compound (3). The reaction time of the third step is usually in the range of 5 minutes to 72 hours.

It is preferable that no water is added into the reaction system of the third step, though water is not generated depending on the reaction in the third step. Specifically, the amount of water contained in the reaction solution in the third step is 0.6 wt % or less, preferably 0.5 wt % or less, more preferably 0.3 wt % or less.

Derivative (1) includes, for example, compounds described in Table 3.

TABLE 3

(1) Pyrazolone structure with Ar, $R^1$, $R^2$ substituents and $H_2N$ group

| Compound number | $-Ar$ | $-R^1$ | $-R^2$ |
|---|---|---|---|
| (1-1) | 2-methylphenyl | $-C(O)S-CH_2-CH=CH_2$ | $-CH(CH_3)_2$ |
| (1-2) | 2,6-dichloro-3-methylphenyl | $-C(O)S-CH_2-CH=CH_2$ | $-CH(CH_3)_2$ |
| (1-3) | 2-methylphenyl | $-C(O)S-CH_2-CH=CH_2$ | $-C(CH_3)_3$ |

TABLE 3-continued (1)

| Compound number | —Ar | —R¹ | —R² |
|---|---|---|---|
| (1-4) | 2,6-dichlorophenyl | —C(=O)S-CH₂-CH=CH₂ | —C(CH₃)₃ |
| (1-5) | 2-methylphenyl | —C(=O)S-CH₂-CH=CH₂ | —CH₃ |
| (1-6) | 2,6-dichlorophenyl | —C(=O)S-CH₂-CH=CH₂ | —CH₃ |
| (1-7) | 2,6-dichlorophenyl | —C(=O)S-CH₂-CH=CH₂ | 4-methylphenyl |
| (1-8) | 2-methylphenyl | —C(=O)S-CH₂-CH=CH₂ | 4-methylphenyl |

According to the present invention, derivative (1) is obtained with good yield. Since generation of a salt represented by the above-described formula (4') is suppressed, there is a preferable tendency that generation of an impurity obtained by exchanging $R^1$ for $R^2$ in derivative (1) is suppressed in the reaction product obtained in the third step. Further, derivative (1) can be obtained with good yield without substituting an ether solvent for a hydrocarbon solvent.

A solution containing a hydrocarbon solvent and derivative (1) obtained by the third step is, for example, subjected to a method such as concentration under reduced pressure of the hydrocarbon solvent and the like, to obtain derivative (1). The resultant derivative (1) may be purified by recrystallization, chromatography and the like.

EXAMPLES

The present invention will be explained further in detail based on examples below. In examples and a reference example, "%" and "parts" are % by weight and parts by weight, respectively, unless otherwise stated. The water content of the reaction solution was determined by the Karl Fischer method.

Example 1

The first step was carried out using an apparatus 910) in FIG. 1. First, FIG. 1 will be explained. A reaction tank (1) is equipped with a jacket so as to be able to heat the tank. The reaction tank (1) is connected to a condenser (3) via pipework (2), and the condenser (3) is connected to a separator (9) via pipework (4). An upper layer (6) of the separator (9) and the reaction tank (1) are connected via pipework 95).

[First Step]

Into the reaction tank (1) were charged 159 parts by weight of xylene and 12.1 parts by weight of lithium hydroxide monohydrate, and pressure reduction was performed until the gauge pressure reached about 10 kPa. Next, the xylene solution in the reaction tank (1) was heated up to about 67° C., to observe that an azeotropic vapor of water and xylene was cooled in the condenser (3) via the pipework (2) and transferred to the separator (9). Xylene separated in the separator (9) was refluxed into the reaction tank (1) via the pipework (5). From a lower layer (7) of the separator (9), 4.7 parts by weight of water was recovered.

The water content of mixture [1] in the reaction tank (1) was 0.19 wt %.

[Second Step]

Next, a solution containing 80 parts by weight of 5-amino-3-oxo-4-O-tolyl-2,3-dihydropyrazole-1-thiocarboxylic acid S-allyl ester (a compound represented by the compound number (2-1) in Table 1), 240 parts by weight of xylene and 80 parts by weight of tetrahydrofuran was dropped from the pipework (8) over a period of 11 hours into the mixture [1] in the reaction tank (1). During dropping, an azeotropic vapor of water and xylene was cooled in the condenser (3) via the pipework 92) and transferred to the separator (9). From the lower layer (7) of the separator (9), 4.7 parts by weight of water was recovered.

Sampling was performed every hour in the reaction tank (1), as a result, the water content was 0.19 to 0.22 wt %.

The solution [2] after completion of dropping was sampled and water was added to the sample and the solution was subjected to liquid chromatography, to find that the proportion of 5-amino-3-oxo-4-O-tolyl-2,3-dihydropyrazole-2-thiocarboxylic acid S-allyl ester (a compound in which Ar represents a 2-methylphenyl group, $R^1$ represents a hydrogen atom and $R^2$ represents $CH_2$—CH—$CH_3$—S—C(=O)— in formula (1), namely, a compound obtained by converting a nitrogen anion of a compound represented by formula (4') into NH) was 1.72% (area of chromatography) based on 100% (area of chromatography) of the proportion of 5-amino-3-oxo-4-O-tolyl-2,3-dihydropyrazole-1-thiocarboxylic acid S-allyl ester corresponding to compound (2). It is understood that a lithium cation is selectively substituted with a hydrogen atom linked to a nitrogen atom at the α-position of a carbonyl group of compound (2).

[Third Step]

into a reaction tank (1") which was different from the above-described reaction tanks (1) and (1') but having the same shape as them, 241 parts by weight of tetrahydrofuran was charged and heated up to 85° C. to cause reflux. Next, into the reaction tank (1"), 273 parts by weight of the solution [2] obtained in the second step (84 parts by weight as 5-amino-3-oxo-4-O-tolyl-2,3-dihydropyrazole-1-thiocarboxylic acid S-allyl ester) and a xylene solution containing 51.9 parts by weight of methanesulfonic acid isopropyl ester were dropped over a period of 1.5 hours, and further, the mixture was refluxed for 20 hours at the same temperature.

The resultant reaction solution was quantified by liquid chromatography (internal standard method), to find a yield of 5-amino-2-isopropyl-3-oxo-4-O-tolyl-2,3-dihydropyrazole-1-thiocarboxylic acid S-allyl ester (a compound in which Ar represents a 2-methylphenyl group, $R^1$ represents an isopropyl group and $R^2$ represents $CH_2$=CH—$CH_2$—S—C(=O)— in formula (1). A compound represented by the compound number (1-1) in Table 3) of 82.3%.

Reference Example 1

Into a reaction tank equipped with a reflux condenser were charged 500 parts by weight of xylene and 105 parts by weight of 5-amino-3-oxo-4-O-tolyl-2,3-dihydropyrazole-1-thiocarboxylic acid S-allyl ester, and the resultant mixture was heated up to about 78° C. Pressure reduction was performed until boiling of the mixture, then, 15.2 parts by weight of lithium hydroxide monohydrate was added while distilling xylene. From the resultant reaction solution, xylene was further distilled at the same temperature over a period of 4 hours (360 parts by weight as the xylene distillation amount).

To the resultant reaction mixture was added water and the solution was subjected to liquid chromatography, to find that the proportion of 5-amino-3-oxo-4-O-tolyl-2,3-dihydropyrazole-2-thiocarboxylic acid S-allyl ester (a compound in which Ar represents a 2-methylphenyl group, $R^1$ represents a hydrogen atom and $R^2$ represents $CH_2$=CH—$CH_2$—S—C(=O)— in formula (1), corresponding to a compound obtained by converting a nitrogen anion of a compound represented formula (4') into NH) was 16.7% (area of chromatography) based on 100% (area of chromatography) of the proportion of 5-amino-3-oxo-4-O-tolyl-2,3-dihydropyrazole-1-thiocarboxylic acid S-allyl ester corresponding to compound (2). It is understood that when xylene was distilled, $CH_2$=CH—$CH_2$—S—C(=O)— linked to the β-position of a carbonyl group in compound (2) was considerably rearranged to the α-position of a carbonyl group.

INDUSTRIAL APPLICABILITY

The present invention is industrially applicable as a method capable of producing derivative (1) with excellent yield.

EXPLANATION OF REFERENCES (1) reaction tank
(2) pipework from reaction tank (1) to condenser (3)
(3) condenser
(4) pipework from condenser (3) to separator (9)
(5) pipework from upper layer (6) of separator (9) to reaction tank (1)
(6) upper layer of separator (9), xylene layer in examples
(7) lower layer of separator (9), water layer in examples
(8) pipework for charging into reaction tank (1)
(9) separator
(10) reaction apparatus

The invention claimed is:

1. A method for producing a salt represented by formula (4):

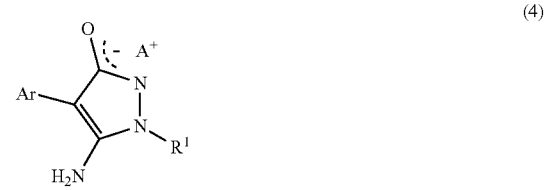

(4)

wherein $A^+$ represents an alkali metal cation, Ar represents an optionally substituted phenyl group, $R^1$ represents an optionally substituted hydrocarbon group, and —$CH_2$— contained in the hydrocarbon group may be replaced by a hetero atom or a carbonyl group, the method comprising a first step of dehydrating a mixture containing a hydrocarbon solvent and an alkali metal hydroxide represented by the following formula:

$A^+ OH^-$ wherein $A^+$ has the same meaning as described above, wherein the mixture contains no compound represented by the following formula (2), and a second step of reacting the mixture dehydrated in the first step with a compound represented by formula (2):

10. A method for producing a pyrazolinone derivative represented by formula (1):

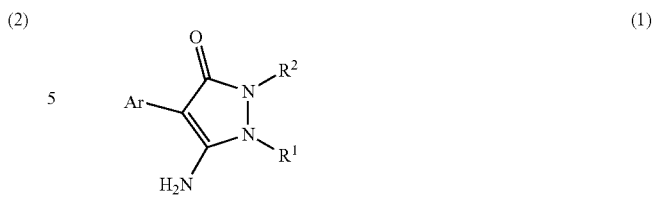

wherein Ar represents an optionally substituted phenyl group, R¹ represents an optionally substituted hydrocarbon group, —CH$_2$— contained in the hydrocarbon group may be replaced by a hetero atom or a carbonyl group, and R² represents an optionally substituted hydrocarbon group, the method comprising a first step of dehydrating a mixture containing a hydrocarbon solvent and an alkali metal hydroxide represented by the following formula:

A⁺ OH⁻ wherein A⁺ represents an alkali metal cation, wherein the mixture contains no compound represented by the following formula (2), a second step of reacting the mixture dehydrated in the first step with a compound represented by formula (2):

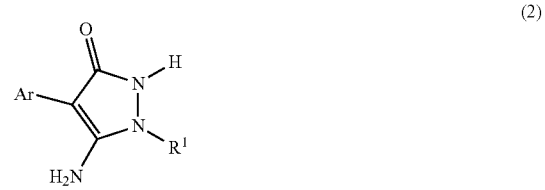

wherein Ar and R¹ have the same meanings as described above, and a third step of reacting the product obtained in the second step with a compound represented by formula (3):

R²—O—SO$_2$R³     (3)

wherein R² has the same meaning as described above and R³ represents an optionally substituted phenyl group or an alkyl group having 1 to 10 carbon atoms.

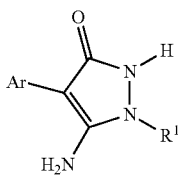

wherein Ar and R¹ have the same meanings as described above.

2. The method according to claim 1, wherein the second step is a step of reacting the mixture dehydrated in the first step with a compound represented by formula (2) while performing dehydration.

3. The method according to claim 2, wherein the second step is a step of reacting the mixture dehydrated in the first step with a compound represented by formula (2) while adjusting the amount of water contained in the reaction solution in the second step to 0.8 wt % or less.

4. The method according to claim 2, wherein the second step is a step of reacting the mixture dehydrated in the first step with a compound represented by formula (2) while performing azeotropic dehydration under reduced pressure at a temperature in the range of 20 to 100° C.

5. The method according to claim 1, wherein the amount of water contained in the mixture dehydrated in the first step is 0.8 wt % or less.

6. The method according to claim 1, wherein the first step is a step of performing azeotropic dehydration under reduced pressure at a temperature in the range of 20 to 100° C.

7. The method according to claim 1, wherein the alkali metal hydroxide is lithium hydroxide.

8. The method according to claim 1, wherein the hydrocarbon solvent is an aromatic hydrocarbon solvent.

9. The method according to claim 1, wherein the second step is a step of reacting the mixture dehydrated in the first step with a compound represented by formula (2) in the presence of an ether solvent.

* * * * *